United States Patent [19]

Austin et al.

[11] 4,097,399

[45] Jun. 27, 1978

[54] PROCESS FOR PREPARING AN OXYALKYLATED PRODUCT

[75] Inventors: Arthur L. Austin, Southgate; William W. Levis, Jr., Wyandotte; Louis C. Pizzini, Trenton; Robert J. Hartman, Southgate, all of Mich.

[73] Assignee: BASF Wyandotte Corporation, Wyandotte, Mich.

[21] Appl. No.: 590,332

[22] Filed: Jun. 25, 1975

Related U.S. Application Data

[62] Division of Ser. No. 425,524, Dec. 17, 1973, Pat. No. 3,957,922.

[51] Int. Cl.² .................... C07F 9/145; C08G 71/04
[52] U.S. Cl. ........................... 252/182; 260/2.5 AJ; 260/2.5 AP; 260/2.5 FP; 260/613 B; 260/615 B
[58] Field of Search ......... 260/615 B, 2.5 FP, 2.5 AJ, 260/2.5 AP, 613 B; 252/182

[56] References Cited

U.S. PATENT DOCUMENTS

| | | | |
|---|---|---|---|
| 2,527,970 | 10/1950 | Sokol | 260/615 B |
| 3,158,580 | 11/1964 | Vandenberg | 260/615 B X |
| 3,158,581 | 11/1964 | Vandenberg | 260/615 B X |
| 3,651,152 | 3/1972 | Umbach et al. | 260/611 B |
| 3,821,316 | 6/1974 | Taniuchi et al. | 260/615 B |

*Primary Examiner*—Benjamin R. Padgett
*Assistant Examiner*—Irwin Gluck
*Attorney, Agent, or Firm*—Gordon W. Hueschen

[57] ABSTRACT

An oxyalkylated product useful for making polyurethane foams is prepared by reacting an alkylene oxide with a heated mixture of a phenol and a non-phenolic active hydrogen compound, at least one of which can be halogenated, in the presence of a catalyst complex of a phenol and an iron or aluminum substance. The mixture can also include a neutral phosphorus compound and/or acid anhydrides to enhance flame retardant properties. Optionally, also, the oxyalkylation reaction can be terminated by adding a tri (lower alkyl) amine and alkylene oxide to react with residual phenolic hydrogen in the mixture.

6 Claims, No Drawings

PROCESS FOR PREPARING AN OXYALKYLATED PRODUCT

This is a division of application Ser. No. 425,524, filed Dec. 17, 1973 now U.S. Pat. No. 3,957,922.

BACKGROUND OF THE INVENTION

This invention relates to oxyalkylated products. More particularly, this invention provides a process for preparing polyol products, and the use thereof in preparing polyurethane compositions.

Polyol products are of interest for making a variety of polymeric products such as polyester and polyurethanes. Polyurethanes have gained widespread acceptance in industry for a variety of uses. Cellular polyurethanes, in particular, are used for a wide variety of purposes, for example, as packaging materials, cushioning and as insulation in the construction industries. Depending upon the uses intended for the products the specifications and costs can vary widely. Some uses of polyurethanes require rigid foams; other uses require semi-rigid or flexible foams. Also, the use of polymeric materials in some cases requires that they have built in flame retardant properties, other uses of polyurethanes do not require extensive burn resistant properties. It would be desirable from both economic and technological viewpoints to have a single process which could be adapted to produce polyol products which meet a variety of product specification and cost requirements, while minimizing undesired side reactions which have occurred. Polyols, including polyoxyalkylation reaction products, are used as an active hydrogen-containing component in polyurethane manufacturing formulations. When flame retardant properties are required in polyurethane foams, it is known to use halogenated compounds and/or derivatives of phosphorus acids as active hydrogen compounds in the polyurethane formulation. Sometimes boron and antimony compounds have been used as additives to the formulation in order to enhance the flame retarding properties of the resulting polyurethane.

While all of the foregoing substances are effective in imparting some degree of flame-resistance to polyurethane plastics, the disadvantage associated with all of these approaches is that the use of increasing quantities of such substances impairs the mechanical and physical properties of the polyurethane product. Also, as the quantity of flame resistance-imparting agents is increased, the problem of blending such agents into the polyurethane formulation is increased.

To be acceptable in the building and construction industry, polyurethane foam spray systems must have a sufficiently low viscosity and must possess a shelf-life of at least six months. The preparation of such polyurethane foam systems is exemplified in U.S. Pat. No. 3,091,551. The flame-resistance of polyurethane foams is evaluated by standard tests, such as the ASTM E-84 Tunnel Test, the Butler Chimney Test and the ASTM D-1692-68 Flame Test. Several methods have been considered by those skilled in the art in an attempt to provide polyurethane foam systems having the above-enumerated properties. Various halogen and/or phosphorus-containing compounds have been employed either as the polyol component of the system or as an additive thereto. See, for example, U.S. Pat. No. 3,364,153.

The usual way for making oxyalkylated polyols for use in making polyurethane foams and polymers has been to use an alkaline catalyst in the polyhydric alcohol/alkylene oxide reaction mixture. However, the resulting polyol reaction mixtures generally contain at least about 0.1 to about 0.5 percent by weight of the alkaline catalyst. Presently steps are taken to remove as much of that alkaline catalyst as possible, preferably down to at least about 5 parts per million because it is known that such alkaline materials in the mixtures interfere with the reaction between the oxyalkylated polyol product and the polyisocyanate in making polyurethanes. Undesired reactions such as gelation of the mixtures occur because of the presence of the alkaline material. It is desirable to provide the polyol and polyurethane making art with an improved, simplified process for making oxyalkylated products which can be used as the polyol reactant in polyurethane manufacture without having to remove substances which limit the utilities of the product or to be concerned with the undesired side reactions caused by alkaline catalyst residues which were carried through with the polyol.

Moore U.S. Pat. No. 2,253,723 discloses the addition of an epoxide to a polyhydric alcohol in the presence of a stannic chloride catalyst. This patent also suggests that similar reactions can be carried out with phenols. Marple U.S. Pat. Nos. 2,327,053 and 2,428,235 disclose the mono-addition of an epoxide to the hydroxy group of an alcohol or phenol in the presence of a metal halide catalyst, and suggests that the formation of secondary or higher products may be favored by decreasing the ratio of the hydroxy compound to the epoxide. MacMullen U.S. Pat. No. 2,401,261 discloses the preparation of solid 2-(pentachlorophenoxy)ethanol from pentachlorophenol and ethylene oxide in Example 1 thereof. Wismer U.S. Pat. No. 3,043,881 discloses the reaction of an epoxyalkyl pentachlorophenyl ether with an aliphatic alcohol in the presence of a Friedel-Crafts catalyst to obtain a mono-ether across the epoxide bond through one hydroxyl group of the aliphatic alcohol. None of the patents disclose the oxyalkylation of mixtures of phenols and non-phenolic active hydrogen compounds, and none of them disclose the use of the catalyst complex system disclosed hereinbelow.

The Austin/Pizzini/Levis U.S. Pat. No. 3,639,541 discloses an ester-containing polyol made by reacting (a) a polyhydroxyl-containing compound, (b) an acid or oxide of phosphorus (c) a halogen-containing organic acid anhydride and (d) an alkylene oxide. In some examples thereof the use of tri-n-butylamine as a catalyst is disclosed. However, the process of that patent and its resulting product is limited in the amount of oxyalkylation that occurs in those mixtures. The amine catalyst permits only 1 molecular equivalent of alkylene oxide to react per available reactive hydrogen, and to that extent that process is somewhat limited in the types of oxyalkylation products that it can produce.

The Pizzini/Levis U.S. Pat. No. 3,639,542 discloses an ester-containing polyol prepared by reacting (a) a neutral phosphate polyol, (b) a halogen-containing organic acid anhydride and (c) propylene oxide. The process of that thereof is limited in the amount of oxyalkylation that takes place in that mixture.

There continues to be a need for more efficient processes, and new economically-obtainable, flame-resistant oxyalkylated products which can be used for a variety of industrial applications, for example, for further reactions with polyisocyanates to make stable pour-inplace, slab stock and sprayable polyurethane foam formulations, for use in making flexible, semi-rigid and rigid foam materials which have applications in the insulation, building and packaging industries.

It is an object of this invention to provide a new, economical process for preparing oxyalkylation polyol products which do not require the use of basic catalysts.

It is a further object of this invention to provide an improved, adaptable process which can be used to prepare oxyalkylation polyol products of a broader range of desired molecular weight and hydroxyl number properties, depending upon the specifications and requirements called for by the use intended for such product.

It is a further object of this invention to provide a process for making an oxyalkylated polyol product which permits more than one mole of alkylene oxide addition per available hydrogen atom in the starting material.

It is a further object of this invention to provide an oxyalkylation polyol producing process in which polyoxyalkylation can be allowed to proceed to the desired degree of physical properties and in which the oxyalkylation reaction can then be controlled by terminating the oxyalkylation when the desired degree of oxyalkylation has taken place.

It is a further object of this invention to provide a simplified process for making phosphorus and halogen-containing oxyalkylated products, which are useful in combination with polyisocyanates for making flame-retardant polyurethane foams.

It is a further object of this invention to provide an improved oxyalkylation process for oxyalkylating mixtures of phenols, non-phenolic active hydrogen compounds and a phenol: aluminum or iron catalyst complex, to obtain substantially acid-free phosphorus and halogen oxyalkylated product mixtures, useful for making polyurethanes.

SUMMARY OF THE INVENTION

Briefly, this invention provides a versatile process for making oxyalkylated products, which are particularly useful in processes for making polyurethane foams to a variety of specifications which comprises forming a mixture of a phenol, a non-phenolic active hydrogen compound and an aluminum or iron substance which forms a complex with phenol when heated therewith, heating the mixture to an efficient oxyalkylation temperature and oxyalkylating the mixture by adding an alkylene oxide thereto until an oxyalkylated product of the desired properties is formed. Preferably, at least one of the phenol or non-phenolic active hydrogen compounds is halogenated. The mixture can also contain a substantially neutral phosphorus compound and/or an organic acid anhydride to enhance flame retarding properties of the oxyalkylated product of the process. When the oxyalkylated product has the desired properties, e.g., the desired average molecular weight or hydroxyl number, the mixture can be vented and heated to remove volatiles from the mixture. The oxyalkylation reaction can be terminated by adding to the oxyalkylation reaction mixture a tris ($C_1$ to $C_4$-alkyl) amine or similar amine to break up the phenol: aluminum or iron complex and alkylene oxide until no further alkylene oxide is reacting in the mixture.

DETAILED DESCRIPTION OF THE INVENTION

According to this invention, a process has been discovered which permits the manufacture of oxyalkylated products of a broader range of physical property variables than was previously possible in an economical manner, and which process permits the use of economical starting materials, more extensive oxyalkylation, if desired, and ready control and termination of the oxyalkylation reaction when that is desired.

This invention also provides a simplified process for providing an oxyalkylated product containing phosphorus and halogen of controlled molecular weight. The new oxyalkylated products of this invention can be used directly in polyurethane making formulations, either as the only active hydrogen component or they can be blended with polyols which contain less or no phosphorus or halogen therein to obtain polyol blends which will impart to the resulting polyurethane foam product the desired degree of flame-retardance or firmness for the use intended. Some uses of polyurethane foams require a higher degree of flame retardance than do others. This invention provides a process for preparing active hydrogen containing oxyalkylated products for accommodating the various uses intended for polyols.

This invention provides an improved process for preparing an oxyalkylated product which comprises
1. providing a mixture containing
   (a) a phenol, at least in an amount sufficient to form a complex with aluminum or iron substance in the mixture,
   (b) a non-phenolic active hydrogen compound having from 1 to 8 active hydrogens per molecule and having an average molecular weight below about 10,000, and
   (c) a substance containing aluminum or iron which will form a complex with phenol,
2. heating the mixture to a temperature in the range of from about 80° C. to about 250° C., and
3. oxyalkylating the heated mixture by adding thereto sufficient alkylene oxide having from 2 to 12 carbon atoms per molecule to form an oxyalkylated product. Preferably at least one of the phenolic or active hydrogen components of the mixture is halogenated.

The oxyalkylation polyol products of this invention are liquid mixtures which have an equivalent weight range of from about 100 to about 3000.

As used herein, the halogen can be fluorine, chlorine, bromine or iodine, but as a practical economic matter, chlorine and bromine are the most economically important for the uses intended for the products of this process.

The reaction mixture can also include a neutral phosphorus compound in an amount sufficient to enhance the flame retarding properties of the oxyalkylated product and of the final products into which the oxyalkylation product may be reacted or utilized. Preferred trivalent phosphorus compounds for use herein are described hereinbelow.

The aluminum or iron substance can be present in any amount which will form a complex with the phenolic component in the mixture and which complex will catalyze the oxyalkylation reaction in the heated mixture. The term "aluminum or iron substance" is used herein to include the aluminum or iron metallic elements, as well as aluminum and iron compounds and composites in various physical and chemical forms. It has been found that all of the aluminum and iron available to us in various physical and chemical forms, some from various commercial sources, which will form a complex with the phenol, at least with the aid of heating to the oxyalkylation temperatures recited herein, will effectively catalyze the oxyalkylation reaction to an extent greater than one mol of alkylene oxide per available active hydrogen in the mixture. Some forms of iron and aluminum are less prone to form complexes with phenol and thus promote little oxyalkylation. Such forms should not be used. However, most readily available and economical forms of aluminum and iron compounds can be used. The concentration of the aluminum or iron substance in the mixture can be from about 50 to about 20,000 parts per million (ppm). Preferably, however, a concentration of from about 250 to about 2,500 parts per million in the mixture to be oxyalkylated is used.

The phenol to active hydrogen compound reactive equivalent ratio in the mixture to be oxyalkylated can be any ratio which will permit oxyalkylation of the heated mixture in the presence of the phenol: aluminum or iron substance complex. Preferably, however, the reactive equivalent ratio in the mixture is from about 4:1 to about 0.1:1 of phenolic hydrogen to Zerewitinoff active hydrogen equivalent in the starting mixtures, and is preferably from about 2:1 to about 1:1 of reactive phenolic hydrogen to Zerewitinoff active hydrogen equivalent.

The phenol:aluminum or phenol:iron substance complex used to catalyze or promote the oxyalkylation in the process of this invention can be prepared prior to mixing it with the phenol and active hydrogen compounds, but it is simpler, more economical, and preferred to add the aluminum or iron substance either per se to the mixture to be oxyalkylated or mixed with the phenol component. Depending upon the source or the process derivation of the phenolic starting material, sometimes enough of an aluminum or iron substance, such as aluminum chloride and/or ferric chloride is present in the phenol initially to permit the oxyalkylation to proceed without adding additional aluminum or iron substances. Useful aluminum and iron compounds which can be used include aluminum and iron salts of economical mineral acids such as aluminum chloride, aluminum sulphate, aluminum nitrate, aluminum phosphate, ferric chloride, ferric sulphate, ferrous chloride, ferrous sulfate, ferrous nitrate, ferric phosphate, and the like. Other examples of useful forms of aluminum and iron compounds include alumina ($Al_2O_3$), organic aluminum compounds such as aluminum stearate and similar aluminum and iron fatty acid salts, aluminum alkoxides, having from about 1 to 12 carbon atoms in each alkoxide group, iron powder, hydrated forms of ferric and ferrous chlorides and sulfates, commercially available iron coated catalyst pellets and powders, and mixed salts such as ammonium aluminum sulfate and mixtures of salts containing aluminum and other metal halides such as a mixture of 1 part by weight of aluminum chloride and 2 parts by weight of stannic chloride but these mixtures are no more effective than the aluminum salt alone. Also mixtures of metallic iron powder and aluminum salts form effective complexes with a phenol. For example, a complex made from a phenol containing from about 250 to 1,000 ppm of a mixture of 1 part metallic iron and 3 parts aluminum chloride promoted extensive oxyalkylation in these reaction mixtures. Metal oxides such as aluminum oxide can be used but they are not preferred where extensive or rapid oxyalkylation is desired. The preferred aluminum and iron compounds for use in this oxyalkylation reaction process mixture are aluminum chloride and ferric chloride.

It has been found, surprisingly, in the studies leading to this invention that other metal and metalloid compounds which have generally been associated or grouped with aluminum and iron compounds in the prior art for catalytic purposes in other chemical mixtures are not nearly as effective in the oxyalkylation reaction mixture system described herein. Compounds of zinc (metal powder, zinc chloride, zinc pellets), cobalt (cobaltous oxide, cobaltic oxide, cobalt chloride, $CoCl_2 \cdot 6H_2O$), tin (tri-n-butyltinmethoxide, stannic chloride, stannous octoate), boric acid ($H_3BO_3$), palladium catalysts, titanium tetrachloride, antimony trichloride, nickel catalyst pellets, copper pellets generally gave substantially inferior oxyalkylation results with non-phenolic active hydrogen compounds in these mixtures.

The process of this invention can be carried out in a conventional polymerization reactor provided with a suitable stirring apparatus, pressure and temperature indicating means, a heat source, and means for introducing alkylene oxide into the reaction vessel and the mixture contained therein. The reaction vessel can be open to the atmosphere and fitted with suitable condensing devices or the reaction vessel can be a pressure vessel. Preferably, the oxyalkylation is carried out in an inert atmosphere and at an elevated pressure. The inert atmosphere can be provided by a nitrogen gas or carbon dioxide blanket to drive air from above the surface of the reaction mixture, or by other conventional means.

The process of this invention can include the step of terminating said oxyalkylation reaction by adding to the oxyalkylated product mixture an effective amount of a tri (lower alkyl) amine having from 1 to 4 carbon atoms, inclusive, in each alkyl moiety thereof in an amount sufficient to catalyze the rapid oxyalkylation of a phenol in the mixture, together with an additional amount of alkylene oxide sufficient to react with any unreacted phenol in the mixture.

When the oxyalkylation reaction is completed, the mixture is vented and heated at atmospheric or reduced pressure to a temperature sufficient to remove undesired volatile material. The mixture can be heated to from about 75° C to about 250° C to remove water, excess or unreacted alkylene oxide, inert gases, alcoholic by-products resulting from any transesterification in the mixture and the like. Any solid materials contained in the liquid oxyalkylated product mixture can be separated by filtering the oxyalkylated product mixture through coarse filter paper.

In the oxyalkylation reaction of the process of this invention it is the phenol:aluminum or iron substance complex which catalyzes the oxyalkylation of the active hydrogen compounds present in the mixture. We do not yet know whether the association between the phenol and the aluminum or iron substance is chemical or physical in nature, or the exact proportions of each which are present in the complex to promote the oxyalkylation reaction in this process. However, we do know that the presence of a phenol alone or the small amount of aluminum or iron substance alone in the absence of a phenol will not catalyze the polyoxyalkylation of these non-phenolic active hydrogen compounds in these mixtures. The amount of phenol:aluminum or iron substance complex which is needed for catalysis is greater than is normally considered as a catalyst level. A mixture of 1 mole of a phenol containing 700 parts per million (ppm) of an aluminum compound with 1 mole of PLURACOL PeP 450 polyol will readily oxyalkylate whereas 0.01 mole of phenol containing 700 ppm of an aluminum compound with 1 mole of PLURACOL PeP 450 polyol will not oxyalkylate to any significant extent.

According to the improved simplified process of this invention, it is not necessary to take steps to remove the metal or metal halide catalyst residues in the oxyalkylated product mixtures. These oxyalkylated products can be used directly as a polyol reactant in making polyurethane foams without the occurrence of the detrimental side reactions which were seen when alkaline catalysts were not removed from the polyols. Thus, this invention offers both time saving process advantages and economical product advantages to the art.

The alkylene oxide can be added with the phenol, non-phenolic active hydrogen compound, and aluminum or iron substance, before heating, but, preferably the alkylene oxide is added to the heated mixture of the phenol/active hydrogen compound/phenol:aluminum or iron substance, and reacted therein until the desired degree of oxyalkylation has occurred. We have also found according to this invention that the extent of oxyalkylation is also dependent upon the choice of active hydrogen compounds which are incorporated into the mixture. In some cases, extensive oxyalkylation will take place in these reaction mixtures. In this process, mono- and dihydric alcohols, and polyhydric alcohol:alkylene oxide adducts made by other methods oxyalkylate extensively so long as there is present sufficient phenol:aluminum or iron substance complex and alkylene oxide to react therewith. However, with judicious selection of the active hydrogen compound, the extent of oxyalkylation will be limited.

We have found, surprisingly, that the oxyalkylation with alkylene oxides of mixtures of phenols with certain polyhydric alcohols having from 3 to about 8 hydroxyl groups per molecule and a molecular weight below about 350 in the presence of these phenol:aluminum or iron substance complexes is cut short or terminated spontaneously after an average of less than about three molar proportions of alkylene oxide are reacted per available hydroxy group even though excess alkylene oxide is available in the reaction mixture. This phenomenon, though not yet fully understood, allows a further variable for use of the process of this invention in designing and controlling the extent of oxyalkylation in the process. In general, the alkylene oxide is added and the oxyalkylation reaction conditions are maintained until samples of the product indicate that the oxyalkylation has progressed to an average of at least 1 mole of alkylene oxide per reactive equivalent of available active hydrogen in the mixture. Preferably, for most uses of the oxyalkylated product this alkylene oxide's available active hydrogen ratio is in the range of from 1 to 5, but it can be higher.

The average molecular weight of the oxyalkylated product can be calculated by the use of the equation:

Average Molecular Weight =
$$\frac{56.1 \times 1000 \times \text{average functionality}}{\text{Hydroxyl number of the product}}$$

The 56.1 is the molecular weight of potassium hydroxide. The average functionality number refers to the average number of active hydrogens per molecule in the active hydrogen component as determined by the Zerewitinoff method. The Hydroxyl number is the number of milligrams of potassium hydroxide equivalent to the hydroxyl content in 1 gram of sample.

The oxyalkylation reaction can be carried out at a relatively wide range of pressures, usually in the range of about 1 atm. to about 10 atm. Preferably the oxyalkylation is carried out at an elevated pressure of about 1 to 8 atm., more preferably at about 3 to 6 atm.

In the commercial scale operations, the reaction is preferably carried out in an inert atmosphere such as nitrogen, carbon dioxide, or the like, so as to minimize color formation due to air oxidation.

The time necessary to carry out the oxyalkylation reaction to the desired degree of completion depends on the specific phenol:aluminum or phenol:iron complex employed, process temperature and pressure, and the desired length of the oxyalkylene chains. The reaction is usually considered complete when the product has an acid number of less than 1. The reaction time can vary from about 30 minutes to about 60 hours or longer, depending on the conditions of reaction but generally should be complete within 10 to 12 hours.

The oxyalkylation reaction can be allowed to proceed vigorously for a desired period of time and then the oxyalkylation can be terminated by adding to the oxyalkylated product mixture of a trialkylamine in an amount sufficient to promote the rapid oxyalkylation of the phenol in the reaction mixture, together with a sufficient amount of alkylene oxide to react with phenolic active hydrogens therein, and sufficient to lower the acid number of the mixture to less than about 1. The amount of tri (lower alkyl) amine added depends somewhat on the stage at which the oxyalkylation is terminated. The amount of added trialkylamine which is added generally will be an amount which is at most approximately equivalent to the original phenol content of the mixture but which is sufficient to promote oxyalkylation of any un-oxyalkylated phenol in the mixture. Sufficient alkylene oxide is added or provided in the mixture until no more alkylene oxide will react in the mixture. Usually the amount of tri (lower alkyl) amine added is in the range of about 1 to about 10 percent by weight of the reaction mixture and preferably about 2 to about 4 percent by weight. The amount of additional alkylene oxide which is added together with or after addition of the tri (lower alkyl) amine is dependent upon the amount of unreacted phenol in the mixture. The phenol:aluminum or iron substance complex is believed to be destroyed by the addition and reaction of alkylene oxide with phenol on a 1:1 reactive equivalent ratio in the presence of the tri (lower alkyl) amine. However, to insure complete reaction we prefer to add between about 1 and 20 percent by weight, more preferably 3 to 10 percent by weight, of alkylene oxide, based on the weight of the reaction mixture. Reaction is allowed to continue until samples of the mixture indicate it has an acid number of less than about 1.

For the purposes of this invention, suitable phenols include phenol, bisphenol A, [2,2-bis(4-hydroxyphenyl)propane], cresols, thymols, xylenol, catechols, quinol and the halophenols such as the chloro-substituted phenols, e.g., pentachlorophenol, 2,4,6-trichlorophenol, the dichlorophenols, tetrachlorophenols, and the like, and the bromo-substituted phenols, e.g., pentabromophenol, 2,4,6-tribromophenol, tetrabromophenol, as well as tetrachlorobisphenol A, tetrabromobisphenol A, and the like.

Suitable non-phenolic active hydrogen compounds for use in the process of this invention are those having from 1 to about 8 active hydrogens per molecule, as determined by the Zerewitinoff method and a molecular weight of from about 32 to about 10,000. The term "Zerewitinoff reagent" is defined in *The Condensed Chemical Dictionary*, Sixth Edition, Reinhold Publishing Company (1956), page 1241. Such compounds include, e.g., alcohols, glycols, amines, thiols and the like as is known in the art. Preferred active hydrogen compounds, as used herein, are compounds which contain 1 to about 8 hydrogens per molecule available for reaction with an alkylene oxide compound in the oxyalkylation process of this invention, and include monohydric, dihydric and polyhydric alcohols and glycols, thiols, amines, ester-polyols as well as their halogenated derivatives and the like. Examples of active hydrogen compounds include alcohols, especially the $C_1$ to $C_6$-alkanols, such as methanol, ethanol, n-propanol, isopropanol, n-butanol, isobutanol, tert-butanol, the pentanols and hexanols, 2-chloroethanol, 2,3-dibromopropanol, ethylene glycol, propylene glycol, the isomeric butylene glycols, 1,5-pentanediol, 1,6-hexanediol, glycerol, trimethylolpropane, 1,2,6-hexanetriol, sorbitol, maltose, sucrose, alpha-methylglucoside, pentaerythritol, 2,2-bis(4-hydroxycyclohexyl)propane as well as numerous others described in the prior art, for example, in U.S. Pat. No. 3,639,541, which is incorporated herein by reference, as well as the corresponding thiols, and aliphatic and aromatic amines such as the alkylamines, particularly the $C_1$ to $C_6$-alkylamines such as methylamine, ethylamine, propylamine, isobutylamine, pentylamine, hexylamine, benzylamine, aniline, the toluidines, and the like the diamines and polyamines such as ethylene diamine, propylene diamines, butylene diamines, phenylenediamines, triethylene tetramine, tetraethylenepentamine, and the like. Mixtures of alcohols, glycols, amines as well as adducts of alkylene oxides with these alcohols, glycols, thiols and amines may also be used as the active hydrogen component starting materials in the process of this invention. Also included as examples of active hydrogen compounds which can be included in the reaction mixture in this invention are the commercially available oxyalkylation products of phosphoric acid as well as trivalent and pentavalent phosphorus esters, phosphines and phosphine oxides containing hydroxyalkyl groups therein. These materials are well known in the polyol literature. Examples include "Fyrol 6" said to have the structure

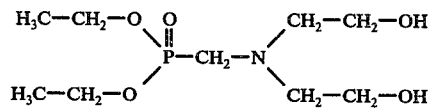

and "Fyrol HMP", said to have the structure

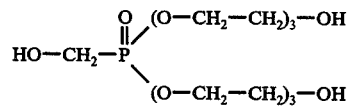

and similar phosphorus-containing polyhydric alcohol active hydrogen compounds. These latter active hydrogen compounds also contribute some phosphorus to the product.

The polyurethane foam spray systems of this invention can be formulated using a "one-shot", "premix" or "prepolymer" procedure. In a "one-shot" procedure, all the foam formulation ingredients are combined at once, as by the use of a multiple stream, multiple orifice nozzle or spray head, or by using an internally mixing type of spray gun having a single orifice. In the "premix" type of procedure, the formulation ingredients are separated into two components, the polyisocyanate component and the polyol component, which components are kept separate until the actual spraying or mixing. In a "prepolymer" procedure, at least a part of the oxyalkylated product is reacted with a polyisocyanate according to conventional procedures to form a liquid prepolymer or semiprepolymer prior to spraying in admixture with the other ingredients. The remaining oxyalkylated product if any, is usually combined with the other foam formulation ingredients prior to the actual mixing or spraying, usually as two separate streams which intimately mix upon impingement.

Regardless of which of the foregoing procedures is utilized to prepare the foam formulation, the foam reactants are deposited intimately mixed upon a supporting surface whereupon substantially immediate foaming and adherence of the generated foam to the supporting surface is achieved.

The details for the manufacture of polyurethanes, in which the herein-described oxyalkylation products can be used, is now well documented in the technical literature and in patents. For example, reference is made to U.S. Pat. No. 3,639,541 and the patents referred to therein for procedures for making polyurethanes from oxyalkylation products. The new oxyalkylation products described herein and the polyurethane products made therefrom are part of this invention.

Polyurethane foam compositions of this invention can be described as comprising, based on the total weight of ingredients, 20 to about 100 parts of an oxyalkylation polyol, prepared as described herein, preferably a polyol which contains both halogen and added phosphorus, incorporated as shown in the detailed examples, 40 to about 60 parts of a polyarylpolyalkylene polyisocyanate having a functionality of about 2.2 to 3.3 or of an isocyanate terminated prepolymer derived from the reaction of a stoichiometric excess of said polyarylpolyalkylenepolyisocyanate with said oxyalkylation polyol, 0.2 to about 2 parts of a wetting agent, and 5 to about 30 parts of a blowing agent. Detailed examples of the foams are given below.

When it is desired to incorporate more phosphorus into the oxyalkylated product to enhance the flame retardant properties, neutral phosphorus esters are preferred. Especially preferred are certain trivalent phosphorus esters. These latter esters may be defined and exemplified as follows:

a trivalent phosphorus ester having a formula selected from the group consisting of

wherein each of $R^1$, $R^2$, and $R^3$ is a hydrocarbon radical free of aliphatic unsaturation containing from 1 to 8 carbon atoms, or such a hydrocarbon radical containing halogen substitution therein, preferably chlorine and/or bromine, and

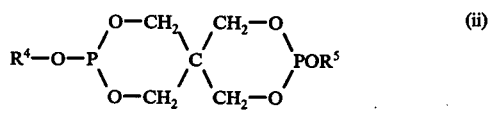

(ii)

wherein each of $R^4$ and $R^5$ is a hydrocarbon radical free of aliphatic unsaturation containing 1 to 8 carbon atoms, or such a hydrocarbon radical containing halogen substitution.

One or more of these compounds can be added to the reaction mixture in an amount sufficient to provide from 1 to about 8 percent by weight of phosphorus in the oxyalkylated product.

Examples of these trivalent phosphorus esters include the aliphatic and/or aromatic phosphites such as trimethylphosphite, triethylphosphite, tri-n-propylphosphite, triphenylphosphite, mixed alkylarylphosphites such as diethyl(phenyl)phosphite, and numerous others satisfying the indicated formula, known in the art. Examples of trivalent phosphorus esters of type (ii) include "dipentite" which is said to be diphenyl pentaerythritol diphosphite, and other similar compounds such as diethyl pentaerythritol diphosphite and the like. Diphosphites are also described in U.S. Pat. No. 2,847,443 and are commercially available. The $R^1$, $R^2$, $R^3$, $R^4$ and $R^5$ radicals in the trivalent phosphorus esters preferably are of lower molecular weight to increase the proportion of phosphorus and any included halogen therein, but these radicals can be represented by alkyl, cycloalkyl, phenyl, alkylphenyl, phenylalkyl, and the halogen substituted radicals of the above type. They are exemplified by methyl, hexyl, cyclobutyl, cyclopentyl, cyclohexyl, phenyl, benzyl, phenethyl, tolyl, and the halogenated derivatives thereof, particularly the chlorinated and brominated groups. Examples of such trivalent phosphorus compounds include tris(2-chloroethyl) phosphite, and tris(2,3-dichloropropyl) phosphite. Other useful phosphorus esters include, for example, dicyclohexyl pentaerythritol diphosphite, dimethyl pentaerythritol diphosphite, and the like. Other phosphorus compounds can be included to supplement or to replace part or all of the phosphorus components in the reaction mixture. However, we have found that these phosphorus esters work best and most economically to obtain the oxyalkylated products of this process.

Suitable alkylene oxides that may be employed are those containing from 2 to about 12 carbon atoms, inclusive, and preferably those containing 2 to 4 carbon atoms inclusive. Both halogenated and non-halogenated alkylene oxides can be used. Examples of useful alkylene oxides include ethylene oxide, propylene oxide, n-butylene oxide, hexylene oxide, octylene oxide, decylene oxide, dodecylene oxides, epichlorohydrin, epibromohydrin, epiiodohydrin, 3,3-dichloropropylene oxide, 3-chloro-1,2-epoxybutane, 3,3,3-trichloropropylene oxide, phenylepoxyethane, 3-phenyl-1,2-epoxypropane and the like. The foregoing alkylene oxides can be used individually or as mixtures. In addition, sometimes it is desired to use one alkylene oxide or mixture thereof to effect oxyalkylation of the heated mixture, and to use a different alkylene oxide toward the end of the oxyalkylation reaction to increase or decrease the reactivity of the oxyalkylated product mixture. For example, it might be advantageous to add 90 weight percent of the alkylene oxide as propylene oxide during the initial oxyalkylation phase, and then to add the last or terminal portion of the alkylene oxide as ethylene oxide to "cap" the oxyalkylated polyol product with more reactive groups.

Optionally, an organic acid anhydride can be also incorporated into the oxyalkylation reaction mixture in order to enhance the flame retardant properties of the produced polyol. The acid anhydride can be present in the reaction mixture in an amount up to about 1:1 mole ratio of phenol to anhydride.

Illustrative of the organic acid anhydrides suitable for use in the process of this invention are dichloromaleic anhydride, tetrabromophthalic anhydride, tetrachlorophthalic anhydride, 1,4,5,6,7,7-hexachloro-bicyclo(2.2.1)-5-heptene-2,3-dicarboxylic anhydride (also known as chlorendic anhydride), 1,4,5,6,7,7-hexachloro-2-methylbicyclo(2.2.1)-5-heptene-2,3-dicarboxylic anhydride, 1,4,5,6,7,7-hexachloro-bicyclo(2.2.1)-5-heptene-2-acetic-2-carboxylic anhydride, 5,6,7,8,9,9-hexachloro-1,2,3,4,4a,5,8,8a-octahydro-5,8-methano-2,3-naphthalene dicarboxylic anhydride, 1,2,3,4,5,6,7,7-octachloro-3,6-methano-1,2,3,6-tetrahydrophthalic anhydride, phthalic anhydride, maleic anhydride, trimellitic anhydride and mixtures of halogenated and non-halogenated anhydrides, and the like.

Examples of tri (lower alkyl) amines which can be used to terminate the oxyalkylation reaction include trimethylamine, triethylamine, tripropylamines, and the tributylamines as well as mixtures thereof.

The relative amounts of the reactants can vary over a wide range depending upon the phosphorus and halogen content and the hydroxyl number and molecular weight desired in the oxyalkylated product mixture. Usually an oxyalkylated product of the present invention intended for use in the manufacture of flame retardant polyurethane would contain about 5 to about 55 percent by weight of halogen and about 0.5 to about 8 percent by weight phosphorus in the product mixture.

The oxyalkylated products containing halogen and phosphorus and prepared in the aforementioned manner are capable of imparting excellent flame resistant properties to polyurethanes such as coatings, foams, and the like, and thus are useful for compounding such formulations. The oxyalkylated products of the present invention whether or not they contain halogen or phosphorus are particularly useful in preparing pour-in-place, slab stock and sprayable polyurethane foam systems which can be used in the insulation, building, and construction industries.

The following examples illustrate the nature of the invention. All parts are by weight unless otherwise indicated.

EXAMPLE 1

Preparation of a Pentaerythritol-Triphenylphosphite-Pentachlorophenol-Propylene Oxide Polyol Triphenylphosphite (63.9 lbs.) is charged into a clean, dry reactor under a nitrogen blanket. Thereafter pentaerythritol (69.1 lbs.) and pentachlorophenol (196.1 lbs.), the latter containing about 750 ppm aluminum and iron compounds, are charged into the reactor, and the reactor sealed and evacuated to about 10 millimeters of mercury. The resulting admixture is then heated to a temperature of about 150° C. and propylene oxide (161.9 lbs.) gradually added thereto with stirring over a time period of about 3 hours while maintaining the pressure within the reactor at about 90 psig or less. After addition of propylene oxide is completed, the reactor contents is maintained at a temperature of about 150° C. for about 2 hours, during which time period the pressure within the reactor reaches a substantially constant value. Thereafter the reactor contents is cooled to a temperature of about 40° to 50° C.

Triethylamine (6.7 lbs.) is added to the cooled reactor contents, the reactor contents then heated to about 90° C., and additional propylene oxide (25.4 lbs.) is charged into the reactor over a time period of about 30 minutes. After addition of propylene oxide is complete, the reactor contents is maintained at 90° C. until the pressure within the reactor levels off. The reactor contents is then stripped to remove volatiles and cooled.

The oxypropylated product contains both phosphorus and chlorine and exhibits the following analysis:

| | |
|---|---|
| Hydroxyl number (phenylisocyanate) | 333 |
| Acid number (potentiometric) | 0.1 |
| Phosphorus, percent by weight | 1.34 |
| Chlorine, percent by weight | 24.6 |
| Nitrogen, percent by weight | 0.12 |
| Refractive Index at 25° C. | 1.536 |
| Brookfield Viscosity at room temperature, cps | 11,000 |

EXAMPLE 2

Preparation of a Phosphorus- and Chlorine-Containing Polyol

Pentaerythritol (956 grams), triphenylphosphite (884 grams), and pentachlorophenol (2,714 grams) containing about 750 ppm of aluminum compound catalyst are charged to a two-gallon autoclave which is then purged and pressure-tested in the usual manner. Thereafter the autoclave is heated and the contents thereof heated to 150° C. During heating the pressure within the autoclave reaches a value of 11 psig.

Propylene oxide (2,240 grams) is added to the heated admixture at a steady rate while the admixture is maintained at 150° C. and the autoclave pressure reaches 90 psig at the end of the oxide addition. After addition of propylene oxide is completed, the autoclave contents is reacted for about 2 hours at 150° C. During the early stages of propylene oxide addition, the resulting reaction is somewhat exothermic and the autoclave is externally cooled to maintain the contents at 150° C.

Thereafter the obtained reaction mixture is cooled to 50° C., triethylamine (29 grams) introduced into the mixture, the resulting mixture heated to 90° C., and additional propylene oxide (95 grams) is charged to the autoclave over a time period of about 30 minutes. The autoclave contents is then maintained at 90° C. for about 2 hours and then stripped for 2 hours at 80° C. and one millimeter of mercury pressure to remove volatiles.

A phosphorus- and chlorine-containing oxypropylated product is produced.

EXAMPLE 3

Oxypropylation of Pentaerythritol — Pentachlorophenol — Triethylphosphite — Tetrabromophthalic Anhydride Admixture A 5-liter flask is equipped with stirrer, thermometer, addition funnel, and reflux condenser. The flask is then charged with pentaerythritol (411 grams), pentachlorophenol (699 grams) containing about 750 ppm of iron compound, tetrabromophthalic anhydride (699 grams), and triethylphosphite (290 grams). The flask contents is then heated to 120° C. and propylene oxide (1,000 grams) added thereto over a four-day period.

Thereafter the obtained reaction mixture is cooled and triethylamine (38 grams) added to the mixture, followed by propylene oxide until the acid number is decreased to less than 1. Then the produced mixture is stripped for 2 hours and 35 minutes at 82° – 85° C. and 1–2 millimeters of mercury. 2941 Grams of an oxypropylated product are obtained having the following properties:

| | |
|---|---|
| Hydroxyl number | 221 |
| Acid number | 0.4 |
| Phosphorus percent by weight | 1.9 |
| Bromine and chlorine meq/g | 6.5 |

EXAMPLE 4

Oxypropylation of Pentaerythritol — Tetrabromobisphenol A — Triphenylphosphite Admixture A 1-liter flask equipped with stirrer, addition funnel, reflux condenser, and a thermometer is charged with pentaerythritol (68 grams), tetrabromobisphenol A (325 grams), triphenylphosphite (54 grams), and anhydrous aluminum chloride (2.3 grams). The flask contents is then heated to 125° C. and propylene oxide added thereto until the acid number is 8.1. At this stage, triethylamine (4 grams) is added and more propylene oxide charged to the flask until the acid number is 0.3. Thereafter the obtained reaction mixture is stripped for 2 hours at 93° C. to 113° C. and 1 millimeter of mercury in order to remove volatiles. 649.7 grams of an oxypropylated polyol product are obtained, having the following properties:

| | |
|---|---|
| Hydroxyl number | 260 |
| Acid number | 0.3 |
| Phosphorus, percent by weight | 0.86 |
| Bromine, percent by weight | 28.7 |

EXAMPLE 5

Oxypropylation of Sucrose — Triethylphosphite — Pentachlorophenol — Tetrabromophthalic Anhydride The following procedure was used in preparing a half-gallon sample of oxypropylated sucrose, triethylphosphite, pentachlorophenol, tetrabromophthalic anhydride polyol as a polyurethane polyol component.

A 5-liter flask, standardly equipped, was charged with 516 grams of sucrose, 428 grams of pentachlorophenol containing about 750 ppm of aluminum and iron compounds, 696 grams of tetrabromophthalic anhydride, 180 grams of triethylphosphite. After heating to 105° C., approximately 1100 ml. of propylene oxide is added over a period of 13 hours at a temperature of 105° to 140° C. 3.16 grams of sodium acetate was added to neutralize the acid in the mixture followed by the addition of 200 ml. of propylene oxide over a 3-hour period. The mixture was then stripped for 2 hours at 80° – 82° C./2 mm. Hg to remove volatiles.

The resulting polyol product weighed 2630 grams, had a hydroxyl number of 306, an acid number of 0.8, contained 1.2 percent phosphorus, and 5.1 meq. of halogen/g of product.

EXAMPLE 6

Reaction of Alpha-Methylglucoside — Triethylphosphite — Pentachlorophenol — Propylene Oxide A 5-liter flask, standardly equipped, was charged with 776 grams of alpha-methylglucoside, 1264 grams of pentachlorophenol containing about 750 ppm of aluminum and iron compounds, 240 grams of triethylphosphite, and heated to 122° C. 1025 ml. of propylene oxide was added at 122° – 138° C. over a 6-hour period. Then 48 grams of triethylamine was added, followed by 265 ml. more of propylene oxide to reduce the acid number to less than 1. The mixture was then stripped for 2 hours at 80° – 85° C./2 mm. Hg to remove volatiles. The oxypropylated product weighed 3827 grams and analyzed as follows:

| | |
|---|---|
| Hydroxyl number | 376 |
| Acid number | 0.7 |
| Phosphorus, percent by weight | 1.5 |
| Halide, meq./g. | 6.43 |

To exemplify utility of these oxyalkylated polyols, this polyol product was formulated with another polyol, PLURACOL polyol 240 (PLURACOL polyol 240 is a propylene oxide adduct of sucrose having a molecular weight of about 780, based upon a hydroxyl number of 575.), in the proportions indicated and the resulting polyol mixture was compounded into polyurethane foam making composition having the proportions of ingredients set forth in the following table:

| Ingredient | Parts by Weight A | Parts by Weight B |
|---|---|---|
| Example 6 polyol | 75 | 85 |
| PLURACOL polyol 240 | 25 | 15 |
| DC-193[1] | 1.5 | 1.5 |
| TMEDA[2] | 1.0 | 1.0 |
| Water | 1.0 | 1.0 |
| Freon 11[3] | 28.0 | 28.0 |
| Polymethylenepolyphenyl isocyanate (Average NCO analysis = 31.5%) | 142.0 | 134.0 |
| NCO/OH | 120/100 | 120/100 |
| Analysis: | | |
| % P w/o Freon 11 | 0.46 | 0.54 |
| % Cl w/o Freon 11 | 7.00 | 8.20 |
| Density, pcf. | 2.12 | 1.95 |
| Compressive strength, psi 10% deflection | 22 | 24 |
| Closed cell count | 66 | 96 |
| Butler Chimney Test % weight retention | 56 | 52 |
| flame height | D | D |
| ASTM D-1692-68 burning time, sec. | 35 | 36 |
| distance consumed, in. | 1.1 | 1.2 |
| Taber friability, cycles/in. | 54 | 172 |

[1]DC-193 is a siloxane-poly(oxyalkylene) ether copolymer surfactant.
[2]TMEDA is tetramethylethylenediamine.
[3]Freon 11 is a trifluorochloromethane.

EXAMPLE 7

Reaction of PLURACOL Polyol 201 — Triphenylphosphite Pentachlorophenol — Tetrabromophthalic Anhydride — Propylene Oxide A 5-liter flask, standardly equipped, was charged with 2000 grams of PLURACOL Polyol 201 (PLURACOL polyol 201 is a propylene oxide adduct of alpha-methylglucoside having a molecular weight of about 520 based upon a hydroxyl number of 430.), 400 grams of triphenylphosphite, 632 grams of pentachlorophenol, containing about 750 ppm of aluminum and iron compounds and 632 grams of tetrabromophthalic anhydride. After heating to over 100° C., 240 ml. of propylene oxide was added over a 2-hour period at temperatures up to 135° C. Then 2.8 grams of sodium acetate was added to neutralize the sulfuric acid contained in the tetrabromophthalic anhydride, followed by 100 ml. of propylene oxide. Then 30 grams of triethylamine was added and then propylene oxide addition continued until the acid number was less than 1. The mixture was stripped for 2 hours at 80° C./2-3 mm. Hg. and filtered to remove solids. The product had the following properties.

| | |
|---|---|
| Hydroxyl number | 281 |
| Acid number | 1.3 |
| Phosphorus, percent by weight | 1.0 |
| Halide, meq./g. | 4.35 |

The resulting polyol was formulated into a polyurethane foam from the ingredients listed below.

| Ingredient | Parts by Weight |
|---|---|
| Example 7 polyol | 100.00 |
| DC-193 | 1.5 |
| TMEDA | 1.0 |
| Water | 1.0 |
| Freon 11 | 23.0 |
| Polymethylenepolyphenyl isocyanate (Average NCO analysis = 31.5%) | 98.0 |
| Analysis: | |
| % P w/o Freon 11 | 0.50 |
| % Br w/o Freon 11 | 5.71 |
| % Cl w/o Freon 11 | 5.21 |
| Density, pcf. | 1.98 |
| Compressive strength, psi 10% deflection | 18 |
| Ingredients | Parts by Weight |
| Taber friability, cycles/in. | 156 |
| Butler Chimney Test % weight retention | 73 |
| flame height | D |
| ASTM D-1692-68 burning time, sec. | 35 |
| distance consumed | 1.1 |

EXAMPLE 8

Reaction of Pentachlorophenol — Pentaerythritol — Triethylphosphite — Propylene Oxide A 5-liter flask was charged with 1330 grams of pentachlorophenol, containing about 750 ppm of aluminum and iron compounds, 680 grams of pentaerythritol and 290 grams of triethylphosphite. The mixture was stirred and heated and volatiles were removed until the temperature was 145° C. Propylene oxide was then added until the acid number was less than 1. Since some solid materials was present 253 grams of pentachlorophenol was added and propylene oxide addition was continued until the acid number was less than 1. The mixture was stripped to remove volatiles and filtered through a coarse paper. The resulting oxypropylated polyol product weighted 3398 grams and had the following properties:

| | |
|---|---|
| Hydroxyl number | 358 |
| Acid number | 0.4 |
| Phosphorus, percent by weight | 1.7 |
| Chlorine, percent by weight | 29.7 |

EXAMPLE 9

Reaction of Pentaerythritol — Triethylphosphite Pentachlorophenol — Tetrabromophthalic Anhydride-Propylene Oxide The following procedure was used in preparing a half-gallon sample of an oxypropylated pentaerythritol-triethylphosphite-pentachlorophenol-tetrabromophthalic anhydride product.

A 5-liter flask, standardly equipped, was charged with 411 grams of pentaerythritol, 699 grams of pentachlorophenol containing about 750 ppm of aluminum and iron compounds, 699 grams of tetrabromophthalic anhydride, and 290 grams of triethylphosphite. After heating to 120° C., 1100 ml. of propylene oxide was added over a 4-day period at a temperature of 100° – 144° C. The acid number at this stage was approximately 6. Then 2.8 grams of triethylamine was added, followed by the addition of propylene oxide at a temperature of 118° – 135° C. to reduce the acid number to less than 1. The mixture was stripped for approximately 3.5 hours at 90° – 102° C./5 mm. Hg pressure. A sample of the oxypropylated polyol product analyzed as follows:

| | |
|---|---|
| Hydroxyl number | 221 |
| Acid number | 0.4 |
| Phosphorus, percent by weight | 1.9 |
| Halide, meq./g. | 6.5 |

EXAMPLE 10

Pentaerythritol — Triphenylphosphite — Triethylphosphite — Pentachlorophenol — Propylene Oxide A 5-liter flask, standardly equipped, was charged with 1596 grams of pentachlorophenol containing about 750 ppm of aluminum and iron compounds, 680 grams of pentaerythritol and a mixture of 195 grams of triethylphosphite and 260 grams of triphenylphosphite that had been heated overnight at 80° C. Then propylene oxide was added until the acid number was less than 1. The mixture was stripped for 2 hours at 90° – 104° C./2–4 mm. Hg. The 3562 grams of oxypropylated polyol product contained a finely divided solid. Upon filtering and washing thoroughly with acetone, approximately 75 grams of the dried solid material was obtained. A sample of the oxypropylated polyol product analyzed as follows:

| | |
|---|---|
| Hydroxyl number | 376 |
| Acid number | 0.6 |
| Phosphorus, percent by weight | 1.77 |
| Chlorine, percent by weight | 24.3 |

The resulting oxypropylated polyol product was formulated into a polyurethane foam composition containing the following ingredients:

| Ingredients | Parts by Weight |
|---|---|
| Example 10 polyol | 100.00 |
| Water | 1.0 |
| DC-193 | 1.5 |
| TMEDA | 1.0 |
| Freon 11 | 25.5 |
| Polymethylenepolyphenyl isocyanate (average NCO analysis = 31.5%) | 125 |

| Ingredients | Parts by Weight |
|---|---|
| Analysis: | |
| % P w/o Freon 11 | 0.77 |
| % Cl w/o Freon 11 | 10.65 |
| Density of foam, pcf. | 2.04 |
| Compressive strength, psi 10% deflection | 17 |
| ASTM D-1692-68 burning time, sec. | 37 |
| distance consumed, in. | 0.8 |
| Butler Chimney Test % weight retention | 80 |
| flame height | 11 |
| Closed cell content, % | 96 |
| Taber friability, cycles, in. | 29 |
| Humid aging at 158° F., 100% Relative Humidity, % volume change | |
| 1 Day | 6 |
| 2 Days | 5 |
| 7 | 8 |
| 14 | 11 |
| 28 | 16 |
| Heat aging at 200° F., % volume change | |
| 1 Day | 3 |
| 2 Days | 4 |
| 7 | 8 |
| 14 | 7 |
| 28 | 15 |
| Low temperature at −20° F., % volume change | |
| 1 Day | −1.5 |

EXAMPLE 11

Pentaerythritol — Triphenylphosphite — Pentachlorophenol — Ethylene Oxide — Propylene Oxide The following procedure was used in the preparation of pentaerythritol-triphenylphosphite-pentachlorophenolethylene oxide-propylene oxide.

An autoclave was charged with 478 grams of pentaerythritol, 442 grams of triphenylphosphite, 1357 grams of pentachlorophenol containing about 750 ppm of aluminum and iron compounds, and 900 grams of ethylene oxide was added dropwise at a temperature of 125° – 145° C. After cooling to 50° C., 30 grams of triethylamine was added and propylene oxide addition continued until a constant reflux was obtained. The autoclave was discharged and the mixture stripped to remove volatiles. The 3389 grams of oxypropylated polyol product had the following properties:

| | |
|---|---|
| Hydroxyl number | 310 |
| Acid number | 0.2 |
| Nitrogen, percent by weight | 0.07 |
| Phosphorus, percent by weight | 1.23 |
| Chlorine, percent by weight | 22.4 |

EXAMPLE 12

Pentaerythritol — Triphenylphosphite — Pentachlorophenol — Ethylene Oxide

The following procedure was used in an autoclave preparation of pentaerythritol — triphenylphosphite — pentachlorophenol — ethylene oxide.

A 1-gallon autoclave was charged with 478 grams of pentaerythritol and 1357 grams of pentachlorophenol containing about 750 ppm of aluminum and iron compounds and 442 grams of triphenylphosphite. After heating to 135° C. 870 grams of ethylene oxide was added at temperatures of up to 150° C. The mixture was reacted for about an hour and then, after cooling to 50°

C., 30 grams of triethylamine was added followed by the addition of 345 grams more of ethylene oxide at up to 125° C. After reacting for approximately 2 hours, the mixture was cooled and discharged. The mixture was stripped for 2 hours at 79° – 81° C./1–2 mm. Hg. A sample of the oxyethylated product had the following analyses.

| Hydroxyl number | 319 |
|---|---|
| Acid number | 0.1 |
| Phosphorus, percent by weight | 1.3 |
| Chlorine, percent by weight | 24.6 |

EXAMPLE 13

Aniline-Pentachlorophenol — Triphenylphosphite — Propylene Oxide

The following procedure was used in the preparation of aniline-pentachlorophenol-triphenylphosphite oxypropylated product.

A 5-liter flask, standardly equipped, was charged with 1330 grams of pentachlorophenol containing about 750 ppm of aluminum and iron compounds, 500 grams of triphenylphosphite and 232.5 grams of aniline. After heating to approximately 125° C., 750 ml. of propylene oxide was added at a temperature up to 150° C. The mixture was then cooled and 35 grams of triethylamine added, followed by oxypropylation at approximately 90° C. until steady refluxing. The product was then stripped for 2 hours at 80° – 82° C./1–2 mm. Hg. The 2931 grams of oxypropylated product had the following properties.

| Hydroxyl number | 192 |
|---|---|
| Acid number | 0.58 |
| Chorine, percent by weight | 28 |
| Phosphorus, percent by weight | 1.73 |
| Nitrogen, percent by weight | 0.69 |
| Viscosity, cps./25° C. | 3250 |

EXAMPLE 14

Pentaerythritol — Dipentite Phosphite — Pentachlorophenol — Propylene Oxide

The following procedure was used in oxypropylating a mixture of pentaerythritol-dipentite phosphite-pentachlorophenol.

A 1-liter flask was charged with 68 grams of pentaerythritol, 62 grams of dipentite phosphite (16% phosphorus), and 192 grams of pentachlorophenol containing about 750 ppm of aluminum and iron compounds. After heating to 125° C., propylene oxide (200 ml.) was added at up to 149° C. After cooling to 81° C., 5 grams of triethylamine was added and oxypropylation continued until the acid number was less than 1. The mixture was stripped for 2 hours at 82° – 87° C./1 mm. Hg. The oxypropylation product filtered readily through No. 1 filter paper. No solid material was recovered. The 478.8 grams of oxypropylation product had the following properties.

| Viscosity, cps./25° C. | 26,800 |
|---|---|
| Hydroxyl number | 345 |
| Acid number | 0.2 |
| Phosphorus, percent by weight | 2.2 |
| Chlorine, percent by weight | 25.9 |

EXAMPLE 15

Dextrose — Triphenylphosphite — Pentachlorophenol — Propylene Oxide

The following procedure was used in oxypropylating a mixture of dextrose-triphenylphosphite-pentachlorophenol.

A 1-liter flask, standardly equipped, was charged with 90 grams of dextrose and 85.2 grams of triphenylphosphite and heated to 140° C. 266 grams of pentachlorophenol containing about 750 ppm aluminum and iron compounds was added. Then propylene oxide was added dropwise with stirring at up to 150° C. After cooling, 4.5 grams of triethylamine was added and oxypropylation continued until the acid number was 0.3. The mixture was then stripped for 3 hours at 84° – 88° C./1 mm. Hg. The 689 grams of oxypropylated product had the following properties.

| Viscosity, cps./25° C. | 5900 |
|---|---|
| Hydroxyl number | 364 |
| Acid number | 1 |
| Phosphorus, percent by weight | 2.4 |
| Chlorine, percent by weight | 24.5 |

EXAMPLE 16

PLURACOL Polyol 240 — Pentachlorophenol — Triethylphosphite — Propylene Oxide

The following procedure was used in studying the reaction of PLURACOL Polyol 240 — pentachlorophenol-triethylphosphite-propylene oxide.

A 1-liter flask, standardly equipped, was charged with 400 grams of PLURACOL Polyol 240, 266 grams of pentachlorophenol containing about 750 ppm of aluminum and iron compounds, 83 grams of triethylphosphite. After heating to approximately 120° C., 80 grams of propylene oxide was added. After adding 5 grams of triethylamine, oxypropylation was continued until the acid number was less than 1. The mixture was stripped for 2 hours at 80° – 91° C./1–2 mm. of Hg. A sample of the oxypropylated product analyzed as follows.

| Hydroxyl number | 312 |
|---|---|
| Acid number | 0.7 |
| Phosphorus, percent by weight | 1.9 |
| Chlorine, percent by weight | 21.2 |

EXAMPLE 17

This example illustrates the use of one of the oxyalkylated products of this invention in making a flame-retardant sprayable polyurethane foam formulation.

The following ingredients were combined to form Component A:

| Ingredients | Parts by Weight |
|---|---|
| Oxypropylated product from Example 1 | 85.0 |
| PLURACOL Polyol 240 | 15.0 |
| Silicone, DC-193 | 1.5 |
| TMEDA | 1.0 |
| Blowing Agent F11B | 27.0 |
| Water, distilled | 1.0 |
| Component B: | |
| Polymethylenepolyphenyl isocyanate (average NCO content = 31.5%) | 136 |

The isocyanate/hydroxyl ratio is 120/100. The TMEDA catalyst and water were added to Component A just prior to mixing Components A and B at 70° – 80° F. The ingredients were run through a Martin Sweets machine to make a polyurethane foam for U.L. tunnel testing. The resulting foam had a core density of 2.41, a compressive yield strength of 33.3 a strength at 10 percent deflection of 31.3, a Taber friability of c/in of 377, had 86.7 percent closed cells (uncorrected), 96.4 percent closed cells (corrected), and gave a rating of 25.6 in a 25 foot tunnel test according to the ASTM F-84 procedure.

EXAMPLE 18

Pentachlorophenol — Triphenylphosphite — Diethanolamine — Propylene Oxide

A 1-liter flask, standardly equipped, was charged with 266 grams of pentachlorophenol containing between 700 and 800 parts per million of aluminum and ferric compounds and 80.3 grams of triphenylphosphite, and then 105.4 grams of diethanolamine was added in increments. By the time the addition of the amine was completed, the temperature had risen to 66° C. and the mixture was extremely viscous. By the time the temperature had increased to 90° C. and approximately 50 ml. of propylene oxide had been added the mixture stirred readily and no further difficulty was encountered. After enough propylene oxide had been added to obtain a low acid number, the product was stripped for three hours at 1–2 mm. Hg from 74° – 98° C. to remove volatiles. The oxypropylated product had a viscosity of 9300 cps at 27° C.

EXAMPLE 19

Tribromophenol — Triphenylphosphite — Aniline-Propylene Oxide — Triethylamine

A 1-liter flask, standardly equipped, was charged with 331 grams of tribromophenol containing between 700 and 800 ppm of aluminum and ferric compounds, 46.5 grams of aniline and 180 grams of triphenylphosphite. After heating the mixture to 130° C., 145 ml. of propylene oxide was added at a temperature up to 155° C. After cooling, 5 grams of triethylamine was added followed by the addition of 80 ml. of propylene oxide at approximately 80° C. The mixture was then stripped of volatile materials at 80° C./1 mm. Hg to remove volatiles. There remained as residue 632.8 grams of oxypropylated product having a hydroxyl number of 170, an acid number of 1.9 and the product contained 38.5 percent bromine and 2.8 percent phosphorus.

EXAMPLE 20

PLURACOL Polyol PeP 450 — Tribromophenol — Pentachlorophenol — Propylene Oxide — Triethylamine A 5-liter flask, standardly equipped, was charged with 1000 grams of PLURACOL Polyol PeP 450 PLURACOL Polyol PeP 450 is a propylene oxide adduct of pentaerythritol having a molecular weight of about 400 based upon a hydroxyl number of 555, 325 grams of tribromophenol, 665 grams of pentachlorophenol and 0.5 gram of aluminum chloride. After heating the mixture to 128° C., 300 grams of propylene oxide was added. Then, after adding 50 grams of triethylamine, propylene oxide was added to continue the oxypropylation until the acid number was less than 1. The mixture was stripped of volatile material by heating at 80° – 85° C./1–4 mm. Hg. for 2 hours. The mixed halogenated oxypropylated product residue weighed 3092 grams and had the following properties.

| | |
|---|---|
| Hydroxyl number | 273 |
| Acid number | 0.3 |
| Total halide, meq./g. | 6.25 |

EXAMPLE 21

Sucrose — Propylene Glycol — Pentachlorophenol — Propylene Oxide — Triethylamine A 5-liter flask, standardly equipped, was charged with 535 grams of sucrose and 190 grams of propylene glycol. The mixture was stirred and heated for several hours at up to 142° C. at which time the last of the solid was in solution. Upon cooling the mixture to 28° C., the mixture was too viscous to stir. However, upon slight reheating the mixture stirred readily. At 137° C. 1330 grams of pentachlorophenol containing about 700 to 800 ppm of aluminum and iron compounds was added. During the addition of the pentachlorophenol the temperature dropped to 81° C. but the mixture still stirred readily. Propylene oxide was added at a temperature of up to 142° C. until the acid number was 1.5. The desired amount of propylene oxide had been added so 13 grams of triethylamine was introduced and then propylene oxide was added to the mixture until steady refluxing occurred. The mixture was heated to strip the volatiles at 82° – 96° C./1–2 mm. Hg. The oxypropylated product weighed 2924 grams. It was filtered through coarse paper and 5.2 grams of unidentified solid was removed. The oxypropylated product had the following properties.

| | |
|---|---|
| Hydroxyl number | 362 |
| Acid number | 0.7 |
| Percent chlorine | 28.7 |

EXAMPLE 22

Dextrose — Glycerine — Pentachlorophenol — Propylene Oxide — Triethylamine

A 1-gallon autoclave was charged with 540 grams of dextrose and 276 grams of glycerine and heated for 2 hours at 130° – 135° C. Then 1596 grams of pentachlorophenol containing about 700 to 800 ppm of aluminum and iron compounds was added. This was followed by the addition of approximately 1000 grams of propylene oxide at 125° C. to effect oxypropylation of the mixture. After cooling to 50° C., 30 grams of triethylamine was added, followed by further oxypropylation with additional propylene oxide at approximately 90° C. until the reaction was completed as indicated by pressure readings. The mixture was then cooled, discharged from the autoclave and stripped of volatile materials, as described above. The polyol product had the following properties:

| | |
|---|---|
| Hydroxyl number | 450 |
| Acid number | 0.1 |
| Percent Chlorine | 27.6 |
| Viscosity, cps./27.5° C. | 6700 |

EXAMPLE 23

PLURACOL Polyol PEP 450 — Tribromophenol — Propylene Oxide — Triethylamine

A 5-liter flask, standardly equipped, was charged with 1400 grams of PLURACOL Polyol PEP 450, defined in Example 20, 1400 grams of tribromophenol and 0.85 grams of aluminum chloride. Then 500 ml. of propylene oxide was added at up to 139° C. to effect oxypropylation of the mixture. After adding 50 grams of triethylamine propylene oxide addition was continued to complete the oxypropylation to an acid number of 0.08. The mixture was then stripped for 2 hours at 81° – 94° C./1–3 mm. Hg. The polyol product weighed 3565 grams and had a viscosity of 2425 centipoise (cps) at 27° C.

EXAMPLE 24

Pentachlorophenol — Dibromopropanol — Propylene Oxide — Triethylamine

A 5-liter flask, standardly equipped, was charged with 1,064 grams of pentachlorophenol containing about 700 to 800 ppm of aluminum and ferric compounds and 436 grams of dibromopropanol. This mixture was heated to 121° C. and propylene oxide was added up to 138° C. After cooling the mixture to approximately 90° C., 32 grams of triethylamine was added followed by propylene oxide until the mixture gave an acid number of 0.13. The mixture was then stripped for 2 hours at 80° – 87° C./1–2 mm. Hg. The polyol product weighed 2566 grams and had a viscosity of 930 cps at 25.5° C.

EXAMPLE 25

Dextrose — Propylene Glycol — Pentachlorophenol — Propylene Oxide

A 5-liter flask, equipped with stirrer, thermometer, addition funnel and reflux condenser, was charged with 450 grams of dextrose and 191.5 grams of propylene glycol. The mixture was heated at up to 130° C. for 1 hour. Then 1330 grams of pentachlorophenol containing about 700 to 800 ppm of aluminum and iron compounds was added. Propylene oxide was then added at 117° – 140° C. to effect oxypropylation until the acid number was less than 1. The mixture was then stripped of volatiles by heating for 2 hours at 80° C./1 mm. Hg. The polyol product had the following properties.

| Hydroxyl number | 3241 |
| --- | --- |
| Acid number | 0.3 |
| Percent chlorine | 30.0 |

EXAMPLE 26

Sucrose — Glycerine — Pentachlorophenol — Propylene Oxide

A 5-liter flask, standardly equipped, was charged with 425 grams of sucrose, and 230 grams of glycerine. The mixture was stirred and heated for 2 hours at 130° – 135° C. and then 1330 grams of pentachlorophenol containing about 700 to 800 ppm of aluminum and iron compounds was added. The mixture was treated with propylene oxide until the acid number was 0.8. After heating the mixture to remove volatiles, the polyol product had the following properties.

| Hydroxyl number | 383 |
| --- | --- |
| Percent chlorine | 27.4 |

EXAMPLE 27

Pentachlorophenol — Aniline — Propylene Oxide

A 1-gallon autoclave was charged with 1862 grams of pentachlorophenol containing about 700 to 800 ppm of aluminum and iron compounds and 326 grams of aniline. After heating the mixture to 129° C., 1365 grams of propylene oxide was added and the mixture reacted to constant pressure. After cooling the mixture to 50° C., the contents were drained from the autoclave. The mixture was then stripped for 2 hours at 89° – 91° C./1 mm. Hg. and filtered through coarse paper. There were no solids. The polyol product weighed 3380 grams and had the following properties.

| Hydroxyl number | 228 |
| --- | --- |
| Acid number | 0.7 |
| Percent chlorine | 36.5 |
| Percent nitrogen | 1.4 |
| Viscosity, cps/28° C. | 14,000 |

EXAMPLE 28

PLURACOL Polyol PeP 450 — Pentachlorophenol Containing a Mixture of Aluminum and Iron Compounds — Phthalic Anhydride — Propylene Oxide A flask equipped with stirrer, thermometer, addition funnel, and reflux condenser was charged with 200 grams of PLURACOL Polyol PeP 450, 133 grams of pentachlorophenol containing between 700 and 800 ppm of a mixture of aluminum and iron compounds and 74 grams of phthalic anhydride. The mixture was stirred and heated for 2 hours at a temperature of 100° C. to 105° C. Then approximately 150 ml. of propylene oxide was added at a temperature of 95° C. to 108° C. over a period of 12 hours. After refluxing for 1.5 hours, the reaction mixture was stripped of volatile materials for 2 hours at a temperature of 88° – 92° C./1–2 mm. Hg. The oxypropylated polyol product mixture weighed 489.3 grams and had the following properties.

| Hydroxyl number | 265 |
| --- | --- |
| Acid number | 0.2 |
| Percent chlorine | 16.8 |

EXAMPLE 29

Phenol — Tetrachlorophthalic Anhydride — Aluminum Chloride — Propylene Oxide A 1-liter flask, standardly equipped, was charged with 94 g. of phenol, 286 g. of tetrachlorophthalic anhydride (TCPA) and 1 g. of aluminum chloride. After heating the mixture to 150° C., propylene oxide was added (dropwise) over an 8.5-hour period. The reaction mixture was then stripped for 2 hours at 80° C. and 1 mm. Hg. pressure. The oxypropylated product residue weighed 564.4 g. and had the following properties.

| Hydroxyl number | 110.6 |
| --- | --- |
| Acid number | 2.7 |

| | |
|---|---|
| -continued | |
| Percent chlorine | 24.1 |

The calculated ratio of reactants was 1 mole of phenol:1 mole of TCPA:3.2 moles of propylene oxide.

EXAMPLE 30

Pentachlorophenol — Phthalic Anhydride and a Mixture of Aluminum and Iron Compounds — Propylene Oxide A 500 ml. flask, standardly equipped, was charged with 133 grams of pentachlorophenol containing about 700 to 800 ppm of a mixture of aluminum and iron compounds, and 74 grams of phthalic anhydride. The mixture was stirred and heated for two hours at 102° C. Then 255 ml. of propylene oxide was added at 89° – 138° C. in approximately a 12-hour period. The product was heated at 79° – 92° C./1–2 mm. Hg. for 1.5 hours to remove volatiles. There remained 380 grams of oxypropylation product which had the following properties.

| | |
|---|---|
| Hydroxyl number | 90.9 – 93.3 |
| Acid number | 1.8 |
| Percent chlorine | 23.9 |

EXAMPLE 31

Pentaerythritol — Pentachlorophenol Containing a Mixture of Aluminum and Iron Compounds and Tetrachlorophthalic Anhydride — Propylene Oxide A 1-liter flask equipped with a stirrer, thermometer, addition funnel and reflux condenser was charged with 63 grams of pentaerythritol, 133 grams of pentachlorophenol containing about 700 to 800 ppm of a mixture of aluminum and iron compounds and 143 grams of tetrachlorophthalic anhydride. The mixture was stirred and heated for approximately 2 hours at 110° – 125° C. Thereafter propylene oxide was added at a temperature of 100° – 125° C. Enough propylene oxide was added to effect oxypropylation to the extent of about 6 moles of propylene oxide to 1 mole of pentaerythritol and 1 mole of pentachlorophenol. The mixture was then heated as before to 1 mm. Hg. to remove volatiles. The product weighed 515.3 grams and had the following properties.

| | |
|---|---|
| Hydroxyl number | 241 – 246 |
| Acid number | 0.3 |
| Percent chlorine | 30.2 |

EXAMPLE 32

PLURACOL Polyol PeP 450 — Tetrabromophthalic Anhydride — Pentachlorophenol Containing a Mixture of Aluminum and Iron Compounds — Propylene Oxide — Triethylamine An autoclave was charged with 1200 grams of PLURACOL Polyol PeP 450, 696 grams of pentachlorophenol containing between 700 and 800 ppm of aluminum and iron compounds, and then 290 grams of propylene oxide was added at 125° – 141° C. Then 28 grams of triethylamine was added followed by 185 grams of propylene oxide at 97° C. After about 2 hours of heating the autoclave was emptied. The contents weighed 3088 grams. A 2987-gram portion was stripped of volatile material for 2.5 hours at 92° – 98° C./2.5 mm. Hg. Since the product had an acid number of 12, a 2779-gram portion was recharged to a flask, treated with 22 grams of triethylamine, and then with 125 ml. of propylene oxide at 80° – 122° C. The mixture was stripped to remove volatiles at 80° – 82° C./1 mm. Hg. for 2 hours. The oxypropylated product residue had the following properties.

| | |
|---|---|
| Hydroxyl number | 262 |
| Acid number | 0.1 |
| Percent halide, meq./g. | 6.13 |

EXAMPLE 33

Pentachlorophenol Containing a Mixture of Aluminum and Iron Compounds — Tetrachlorophthalic Anhydride — Propylene Oxide — Triethylamine A reaction flask was charged with 1197 grams of pentachlorophenol containing between about 700 and 800 ppm of aluminum and iron compounds, 1608 grams of tetrachlorophthalic anhydride, and 390 ml. of propylene oxide and then heated at 110° C. At that temperature propylene oxide addition was continued. After 1510 ml. of propylene oxide was added, 42.7 grams of triethylamine was added and then propylene oxide addition was continued until the acid number of the mixture was less than 1. The mixture was stripped for 2 hours at 86° – 91° C./1 mm. Hg. to remove volatiles. The oxypropylated product residue had the following properties.

| | |
|---|---|
| Hydroxyl number | 113.9 |
| Acid number | 0.7 |
| Percent chlorine | 40.2 |

EXAMPLE 34

This example illustrates and compares the differences in oxyalkylation of (A) a monohydric alcohol, (B) and (C) dihydric alcohols, and (D) a trihydric alcohol under similar reaction conditions.

A. OXYPROPYLATION OF N-BUTANOL AND PENTACHLOROPHENOL

A 1-liter reaction flask was charged with 37 grams (0.3 mole) of n-butanol and 133 grams (0.5 mole) of pentachlorophenol containing between 700 and 800 ppm of aluminum and iron compounds. After heating the mixture to 129° C., 770 ml. of propylene oxide was added over an 8-hour period at a temperature of 120° – 170° C. Then 446 grams of the 806.7 grams of oxypropylated reaction mixture was transferred to a 1-gallon autoclave and oxypropylation with additional propylene oxide was continued for 8 hours at a temperature of 145° – 155° C. (A total of 1810 grams of propylene oxide had been added.) A 509.6-gram portion of the resulting oxypropylated reaction mixture was stripped of volatile materials by heating at 98° – 160° C. at 1 mm Hg. for 2 hours. The oxypropylated product residue weighed 379.7 grams, had a hydroxyl number of 51.6, an acid number of 0.5 and contained 3.3% chlorine. The calculated ratios of reactants were 1 mole of butanol to 1 mole of pentachlorophenol to 50.5 moles of propylene oxide or 50.5 moles of propylene oxide per available hydroxyl group.

B. OXYPROPYLATION OF PROPYLENE GLYCOL AND PENTACHLOROPHENOL

A 1-liter flask was charged with 38 grams (0.5 mole) of propylene glycol and 133 grams (0.5 mole) of pentachlorophenol containing between 700 and 800 ppm of aluminum and iron compounds. The mixture was heated and 614 grams of propylene oxide was added over a 6-hour period at 140° – 160° C. Then a 752-gram portion of the resulting oxypropylated mixture was transferred to an autoclave and the mixture was treated therein with 1685 grams of propylene oxide at 143° – 149° C. over a 10.5-hour period to effect additional oxypropylation. The resulting reaction mixture still had an acid number higher than 1 so a 553-gram portion of this mixture was recharged to an autoclave and 145 grams of propylene oxide was added thereto over 2.5 hours at 145° – 150° C. After reacting for an hour at 149° C., a 701-gram portion of the resulting oxypropylated material was discharged and a 643-gram portion thereof was stripped for 2.5 hours at 1–2 mm. Hg. at 97° – 149° C. to remove volatile material. The oxypropylated product residue weighed 500.2 grams and had the following properties.

| Hydroxyl number | 57.8 |
|---|---|
| Acid number | 0.4 |
| Percent chlorine | 2.9 |

The calculated ratios were 1 mole of propylene glycol, 1 mole of pentachlorophenol, to 117.8 moles of propylene oxide, or 39 moles of propylene oxide per available OH group.

C. OXYPROPYLATION OF TRIPROPYLENE GLYCOL AND PENTACHLOROPHENOL

A 1-liter flask was charged with 96 grams (0.5 mole) of tripropylene glycol and 133 grams (0.5 mole) of pentachlorophenol containing between 700 and 800 ppm of aluminum and iron compounds. The mixture was heated and 390 ml. of propylene oxide was added in 2.33 hours at a temperature of from 151° – 160° C. The oxypropylated product mixture at this point had an acid number of 45.4 and the ratio of reactants was calculated as 1 mole of tripropylene glycol to 1 mole of pentachlorophenol to 11 moles of propylene oxide or 3.6 moles of propylene oxide per available hydroxyl group. More propylene oxide could have been added.

D. OXYPROPYLATION OF GLYCERINE AND PENTACHLOROPHENOL

A 1-liter flask, standardly equipped, was charged with 133 grams of pentachlorophenol containing between 700 and 800 ppm of aluminum and iron compounds and 46 grams of glycerine. Propylene oxide was then added over a 25-hour period while heating the mixture at up to 153° C. until steady refluxing occurred. The reaction mixture was then stripped of volatile materials for 2 hours at 80° – 89° C., 1–2 mm. Hg. pressure. The resulting product residue weighed 360.8 grams and had the following properties.

| Hydroxyl number | 305 |
|---|---|
| Acid number | 0.2 |
| Percent chlorine | 22.7 |

The calculated ratio of reactants was 1.56 moles of propylene oxide per hydroxyl group.

EXAMPLE 35

Oxypropylation of Pentaerythritol and Pentachlorophenol

A 1-liter flask was charged with 133 grams (0.5 mole) of pentachlorophenol containing between 700 and 800 ppm of aluminum and iron compounds and 68 grams (0.5 mole) of pentaerythritol. The mixture was heated and 211 ml. of propylene oxide was added in 21.5 hours at 118° – 170° C. The resulting oxypropylated reaction mixture was heated at 100° – 125° C. for two hours at 2 mm. Hg. to remove volatiles. The oxypropylated product residue weighed 325.9 grams and had the following properties.

| Hydroxyl number | 377 |
|---|---|
| Acid number | 0.4 |
| Percent chlorine | 24.7 |

The calculated ratios were: 1 mole of pentaerythritol, 1 mole of pentachlorophenol and 4.3 moles of propylene oxide, or 0.86 moles of propylene oxide per available hydroxyl group.

EXAMPLE 36

Oxypropylation of Sucrose and Tetrachlorophenol

A 1-liter flask was charged with 43 grams of sucrose and 116 grams of tetrachlorophenol containing between 600 and 700 ppm of aluminum and iron compounds. The mixture was stirred and heated for about 3 hours at up to 105° C. Propylene oxide was added at 90° – 133° C. over a 70-hour period until steady refluxing occurred. The oxypropylated reaction mixture was heated for 2 hours at 84° – 94° C./2 mm. Hg. to remove volatiles. The resulting oxypropylated product residue weighed 224.4 grams and had the following properties.

| Hydroxyl number | 297 |
|---|---|
| Acid number | 1.1 |
| Percent chlorine | 38.4 |

The calculated ratios were 1 mole of sucrose to 4 moles of tetrachlorophenol to 9 moles of propylene oxide, or 0.75 moles of propylene oxide per available hydroxyl group.

EXAMPLE 37

Oxypropylation of Sorbitol and Pentachlorophenol

A 1-liter flask was charged with 91 grams (0.5 mole) of sorbitol and 133 grams (0.5 mole) of pentachlorophenol containing between 700 and 800 ppm of aluminum and iron compounds. After heating the mixture at 125° C. for about 1 hour, 240 ml. of propylene oxide was added in approximately 30 hours at a temperature of from 100° – 145° C. The oxypropylated reaction mixture was stripped of volatiles by heating for 2 hours and 25 minutes at 82° – 98° C./1 mm. Hg. The resulting oxypropylated product residue weighed 354.4 grams and had the following properties.

| Hydroxyl number | 530 |
|---|---|
| Acid number | 0.1 |

| | -continued |
|---|---|
| Percent chlorine | 34.6 |

The calculated ratios were 1 mole of sorbitol to 1 mole of pentachlorophenol to 4.5 moles of propylene oxide or 0.64 moles of propylene oxide per available hydroxyl group.

EXAMPLE 38

Oxypropylation of Glycerine and Pentachlorophenol

A 1-liter flask was charged with 92 grams (1 mole) of glycerine and 133 grams (0.5 mole) of pentachlorophenol containing between 700 and 800 ppm of aluminum and iron compounds. The mixture was heated and 465 ml. of propylene oxide was added at 127° – 160° C. over 18 hours. After allowing the mixture to react for several additional hours at 122° – 160° C., the oxypropylated reaction mixture was stripped for 2 hours at 87° – 93° C./2 mm. Hg. The resulting oxypropylated product residue weighed 484.7 grams and had the following properties.

| Hydroxyl number | 376 (phthalation) |
|---|---|
| | 392 (acetylation) |
| Acid number | 0.6 |
| Percent chlorine | 18.4 |

The calculated ratios were 2 moles of glycerine to 1 mole of pentachlorophenol to 8.9 moles of propylene oxide or 1.3 moles of propylene oxide per available hydroxyl group.

EXAMPLE 39

Oxypropylation of a 1:2 Mole Ratio Glycerine: Pentachlorophenol

A 1-liter flask was charged with 23 grams (0.25 mole) of glycerine and 133 grams (0.5 mole) of pentachlorophenol containing between 700 and 800 ppm of aluminum and iron compounds. The mixture was heated and 744 ml. of propylene oxide was added in 7 hours at a temperature of 126° – 170° C. At this time the acid number was still 24.2. The calculated ratios were 0.25 mole of glycerine to 0.5 mole of pentachlorophenol to 10.3 moles of propylene oxide or 8.2 moles of propylene oxide per available hydroxyl group.

EXAMPLE 40

Oxypropylation of Glycerine and Pentachlorophenol in Presence of Large Excess of Aluminum Chloride A 1-liter flask was charged with 92 grams (1 mole) of glycerine and 133 grams (0.5 mole) of pentachlorophenol containing between 700 and 800 ppm of aluminum and iron compounds and 4 grams of aluminum chloride. The mixture was heated and 190 ml. of propylene oxide was added in 6 hours at 131° to 160° C. The resulting mixture was stripped of volatile materials by heating for 2 hours at 100° – 115° C./2 mm. Hg. The oxypropylated product residue weighed 353.2 grams and had the following properties.

| Hydroxyl number | 527 |
|---|---|
| Acid number | 0.6 |
| Percent chlorine | 26.8 |

The calculated ratios were 2 moles of glycerine to 1 mole pentachlorophenol to 8.28 moles of propylene oxide or 1.18 moles of propylene oxide per available hydroxyl group.

In some of the Examples wherein a halophenol containing aluminum and iron compounds is used in the reaction mixture, the aluminum and iron may be present therein in the form of the respective aluminum halide or iron halide salt. The analysis of the phenol for aluminum and iron content is done by gravimetric methods and spectrographic analysis of the ash of the phenolic sample. The presence of aluminum and iron substances is confirmed by the spectrograph. The amount thereof is calculated from the ash but the chemical or physical form of the aluminum and iron substance in those phenol starting materials has not yet been established with certainty. Therefore, in such cases, they are referred to herein generally as aluminum and iron compounds.

For some combinations of reactants, particularly where one of the starting materials is a solid at the working atmospheric temperature it may be desirable to include a diluent or solvent in the reaction mixture to serve as a means to disperse the solid material to a transportable form and to provide a means for dispersing heat of reaction. Such diluent is preferably a solvent for any such solid reactant and is sufficiently volatile that it can be removed during the final stripping step with excess reactants, water, alcohol by-products, and the like. Examples of such solvents or diluents include aromatic hydrocarbons such as benzene, toluene, xylene, aliphatic and cycloaliphatic hydrocarbons such as pentane, hexane, heptane, cyclopentane, cyclohexane, ethers such as diethyl ether, diisopropyl ether, tetrahydrofuran, dioxane, esters such as ethyl acetate, propyl acetate, propylene glycol diacetate, and halogenated hydrocarbons such as methylene chloride, ethylene chloride, ethylene dichloride, trichloroethylene, chlorobenzene, and the like.

We claim:
1. Process for preparing an oxyalkylated product which comprises
   1. providing a mixture containing
      a. a phenol, at least in an amount sufficient to form a complex with an aluminum or iron substance in the mixture,
      b. a non-phenolic active hydrogen compound having 2 to 8 active hydrogens per molecule and having an average molecular weight below about 10,000,
      c. a substance containing aluminum or iron which will form a complex with phenol, and
      d. an organic acid anhydride, at least one of which components (a), (b), and (d) is halogenated,
   2. heating the mixture to a temperature in the range of from about 80° C. to about 250° C., and
   3. oxyalkylating the heated mixture by adding thereto sufficient alkylene oxide having from 2 to 12 carbon atoms to form an oxyalkylated polyol product.
2. Process of claim 1 wherein each of the phenol (a), the active hydrogen compound (b), and the organic acid anhydride (d) is halogenated.
3. Process of claim 1 which further includes the step of terminating the oxyalkyation of the mixture by adding to the mixture a tri (lower alkyl) amine having from 1 to 4 carbon atoms in each alkyl group in an amount which is at most approximately equivalent to the original phenol content of the mixture but which is sufficient in amount to promote oxyalkylation of any un-oxyalkylated phenol in the mixture, and additional alkylene oxide until no more alkylene oxide will react in the mixture.

4. An oxyalkylated polyol prepared by the process of claim 1.

5. An oxyalkylated polyol prepared by the process of claim 2.

6. An oxyalkylated polyol prepared by the process of claim 3.

* * * * *

UNITED STATES PATENT AND TRADEMARK OFFICE
CERTIFICATE OF CORRECTION

PATENT NO. : 4,097,399

DATED : June 27, 1978

INVENTOR(S) : Austin et al.

It is certified that error appears in the above-identified patent and that said Letters Patent are hereby corrected as shown below:

[56] References Cited, U.S. Patent Documents; U.S. Patent Documents, attachments to paper 6, are not published in the patent. Three (3) documents are missing, they are,
--3,642,646   2/1972   Marcus . . . . 252/182
  3,833,526   9/1974   Cear et al. . . 252/182
  3,875,183   4/1975   Papa et al. . . 252/182--

Col. 8, line 59; "purposes" should read --purpose--

Col. 19, Table of Example 13, line 3: "Chorine," should read --Chlorine,--

Col. 21, lines 59-61; "PLURACOL Polyol PeP 450 is a propylene oxide adduct of pentaerythritol having a molecular weight of about 400 based upon a hydroxyl number of 555" should read--(PLURACOL Polyol PeP 450 is a propylene oxide adduct of pentaerythritol having a molecular weight of about 400 based upon a hydroxyl number of 555.)--

Signed and Sealed this

Nineteenth Day of December 1978

[SEAL]

Attest:

RUTH C. MASON
Attesting Officer

DONALD W. BANNER
Commissioner of Patents and Trademarks